United States Patent [19]

Mastrototaro

[11] Patent Number: 5,299,571
[45] Date of Patent: Apr. 5, 1994

[54] APPARATUS AND METHOD FOR IMPLANTATION OF SENSORS

[75] Inventor: John J. Mastrototaro, Indianapolis, Ind.

[73] Assignee: Eli Lilly and Company, Indianapolis, Ind.

[21] Appl. No.: 8,611

[22] Filed: Jan. 22, 1993

[51] Int. Cl.⁵ .................................................. A61B 5/00
[52] U.S. Cl. ..................................... 128/634; 128/637
[58] Field of Search ......................... 604/52, 49, 51; 128/180, 632, 637, 634, 635

[56] References Cited

U.S. PATENT DOCUMENTS

| | | | |
|---|---|---|---|
| 3,224,433 | 12/1965 | Hroch von Dalebor | 128/635 |
| 3,224,436 | 12/1965 | Le Massena | 128/635 |
| 4,294,258 | 10/1981 | Bernard | 128/635 |
| 4,340,457 | 7/1982 | Kater | 128/635 X |
| 4,403,984 | 9/1983 | Ash et al. | 128/632 X |
| 4,417,886 | 11/1983 | Frankhouser et al. | 604/53 |
| 4,935,008 | 6/1990 | Lewis, Jr. | 604/52 |

FOREIGN PATENT DOCUMENTS 259951  3/1988  European Pat. Off. ............ 128/634

OTHER PUBLICATIONS

Arrow International, Inc.—Brochure for Arrow Twin Cath (1989).

Primary Examiner—Gene Mancene
Attorney, Agent, or Firm—Woodard, Emhardt, Naughton, Moriarty & McNett

[57] ABSTRACT

An apparatus for implantation of in vivo sensors includes a housing, a dual-lumen tube extending therefrom, and an in vivo sensor received within one of the lumen of the tube. A needle is received within the other lumens of the tube, and is used to insert the tube through the skin. After implantation, the needle is removed, and the flexible tube and sensor remaining beneath the skin provides the user with reduced irritation and greater comfort. The associated method for subcutaneous implantation of a sensor for use in vivo is also disclosed.

21 Claims, 2 Drawing Sheets

APPARATUS AND METHOD FOR IMPLANTATION OF SENSORS

BACKGROUND OF THE INVENTION

1. Field of the Invention

The present invention relates to an apparatus and method for implantation of an in vivo sensor, and particularly to a minimally invasive method for implanting a sensor.

2. Description of the Prior Art

Certain sensors, such as glucose sensors, are intended for use in vivo, requiring that the sensors be implanted in a fashion consistent with their use. However, it is also desirable that the method of implantation be quick, easy and convenient. The method of implantation is advantageously one which is readily performed both by medical personnel administering to a patient, and also by the person being monitored. Since this person likely will not have medical training, the method should be one which can be performed reliably, such that the readings from the sensor are accurate.

The present invention provides a method which is readily performed for the implantation of a glucose or other sensor, and which uses an apparatus which provides quick and reliable results. While devices have existed for introducing a catheter into small vessels subcutaneously, the introduction of in vivo sensors in this manner has not been suggested.

In U.S. Pat. No. 4,417,886, issued to Frankhouser et al. on Nov. 29, 1983, there is disclosed a catheter introduction set. The Frankhouser patent describes an assembly including a catheter mounted on an introducer needle, with the tip of the needle extending slightly beyond the end of the catheter. A wire guide is received within the needle and attached to a guide tube extending rearwardly from the needle. In use, the needle is inserted into the lumen of the vessel, the spring wire guide is advanced into the vessel, and the catheter is then advanced forwardly to track the spring wire guide into the vessel to the desired position. Thereafter, the spring wire guide and needle are removed.

A comparable device, but without the wire guide, is currently marketed by MiniMed Technologies of Sylmar, Calif. under the name SOF-SET. This device includes a 24 gauge needle received within a short 24 gauge catheter. The needle includes a handle, and is used to introduce the catheter into the body by piercing through the skin. The catheter extends from a support adapted to be secured to the skin. A length of tubing also extends from the support, and communicates with the catheter upon withdrawal of the needle.

Methods and assemblies for the introduction of dual lumen catheters have also been identified. Dual lumen catheters have been noted as providing two means for access to a vessel, such as for withdrawal of blood samples and the infusion of drugs. An introducing needle assembly similar to that described in the Frankhouser patent, but including a double lumen needle, is disclosed in U.S. Pat. No. 4,935,008, issued to Lewis on Jun. 19, 1990. Similarly, the TWIN CATH® product from Arrow International, Inc., comprises an introducer including a two lumen catheter. One lumen of the catheter is round and receives a needle therein, and the other lumen has a C-shaped cross section and surrounds a portion of the round lumen.

SUMMARY OF THE INVENTION

Briefly describing one aspect of the present invention, there is provided an apparatus for implantation of a sensor which comprises a housing, a dual-lumen tube attached to the housing, a sensor received within a first lumen of the tube, and a needle received within the second lumen of the tube. The tube and needle are sized such that the needle is inserted under the skin to the level of the housing, providing a desired placement of the sensor. The needle is then removed and the remainder of the apparatus is secured against the skin during the time that monitoring with the sensor is desired. A related method for implanting an in vivo sensor is also provided.

It is an object of the present invention to provide a simple, quick and reliable apparatus and method for implantation of an in vivo sensor. A further object of the present invention is to provide an apparatus and method which reliably places an in vivo sensor in a desired position beneath the user's skin. Further objects and advantages of the present invention will be apparent from the drawings and description of the preferred embodiment which follows.

DESCRIPTION OF THE PREFERRED EMBODIMENT

Figure 1:
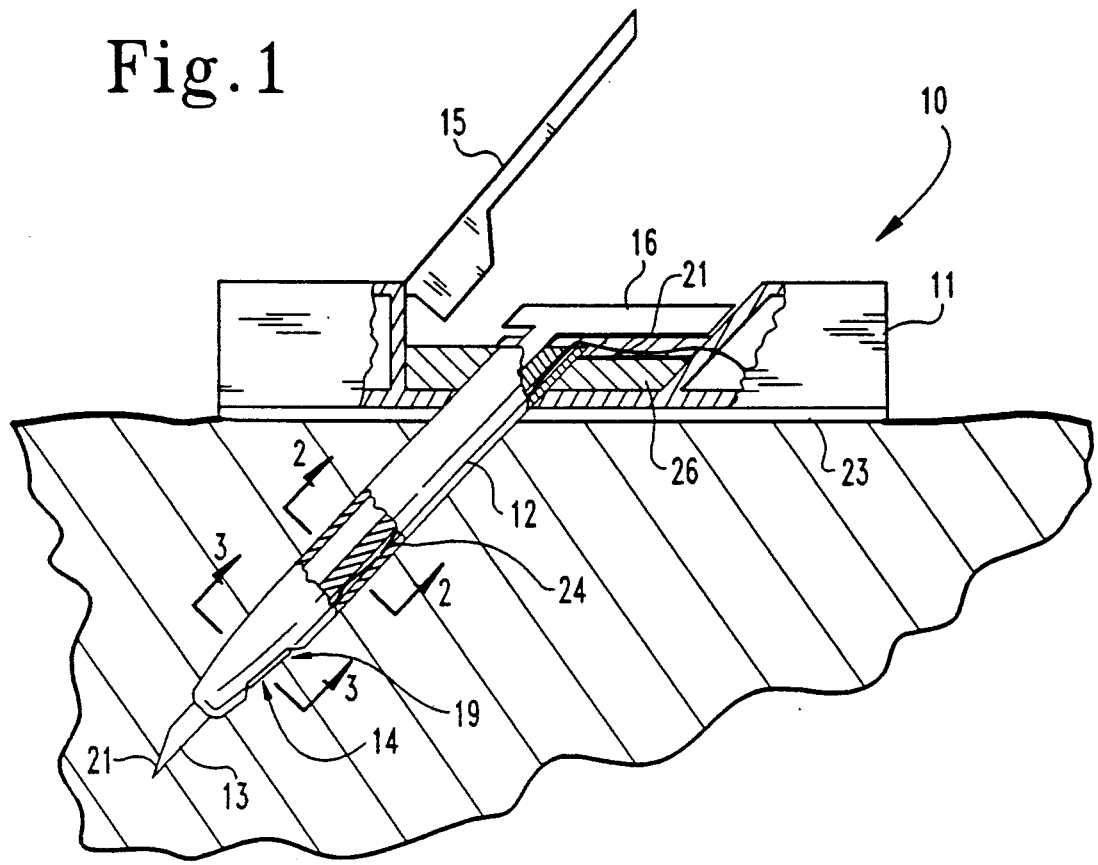
FIG. 1 is a side, partially cross-sectional view of an apparatus for the subcutaneous implantation of an in vivo sensor constructed in accordance with the present invention.
Figure 2:
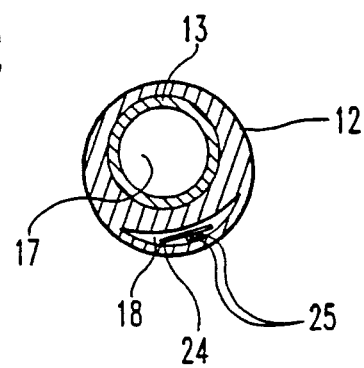
FIG. 2 is a cross-sectional view of the dual-lumen tube useful in the present invention, taken along the line 2—2 in FIG. 1 and looking in the direction of the arrows.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention provides an efficient and easy to use apparatus and method for implanting in vivo sensors. The apparatus is simple in construction and may be readily used by medical personnel or by the user of the sensor. This apparatus and method have wide spread application for use with sensors adapted for implantation in this manner. By way of example, the invention is described with respect to use with glucose sensors, but the invention is not limited to use with these types of sensors.

Referring in particular to the drawings, there is shown an apparatus 10 for subcutaneous implantation of a sensor. The apparatus includes a housing 11 and a dual lumen tube 12 attached thereto and extending outwardly of the bottom surface thereof. A needle 13 is received within one of the lumen of the tube 12, and a sensor 14 is received within the other lumen. The needle is used to introduce the tube subcutaneously, and is thereafter removed, leaving the tube and the sensor 14 retained beneath the skin for use.

The housing 11 provides several functions with respect to the overall implantation apparatus. The housing comprises a lightweight structure which supports the tube 12 and contains the needle 13 prior to use. In a preferred form, the housing includes a cover 15 which provides access to the proximal end of tube 12, and therefore to the needle 13. The needle includes a handle 16 to facilitate its removal from the tube 12 after implantation has been accomplished. The housing 11 defines a cavity within which the handle is received, and which is accessed by opening the cover 15. The cover also closes the cavity and therefore the proximal end of the tube 12 after the needle has been removed and while the sensor is in use.

Attached to the housing at its proximal end is the dual-lumen tube 12. This tube defines a first lumen 17 and a crescent-shaped, second lumen 18. The first lumen is preferably round and receives the needle 13 therein. The sensor 14 is received within the second lumen 18. Preferably, the tube 12 includes an opening 19 at the distal end. The sensor 14 includes a sensing element 20 which is positioned within the opening 19 to be exposed exteriorly of the tube.

The needle 13 is used for inserting the tube 12 and associated sensor 14 beneath the surface of the skin. The needle has a pointed distal tip 21 for piercing the skin. The tube 12 includes a distal end 22 having an external surface which tapers inwardly in the distal direction, thus presenting a low profile for insertion through the skin. The tapering of the distal end of the tube is conveniently accomplished by "pulling down" the tube over the needle. The pointed tip of the needle extends a slight distance outwardly of the distal end of the tube.

Figure 4:
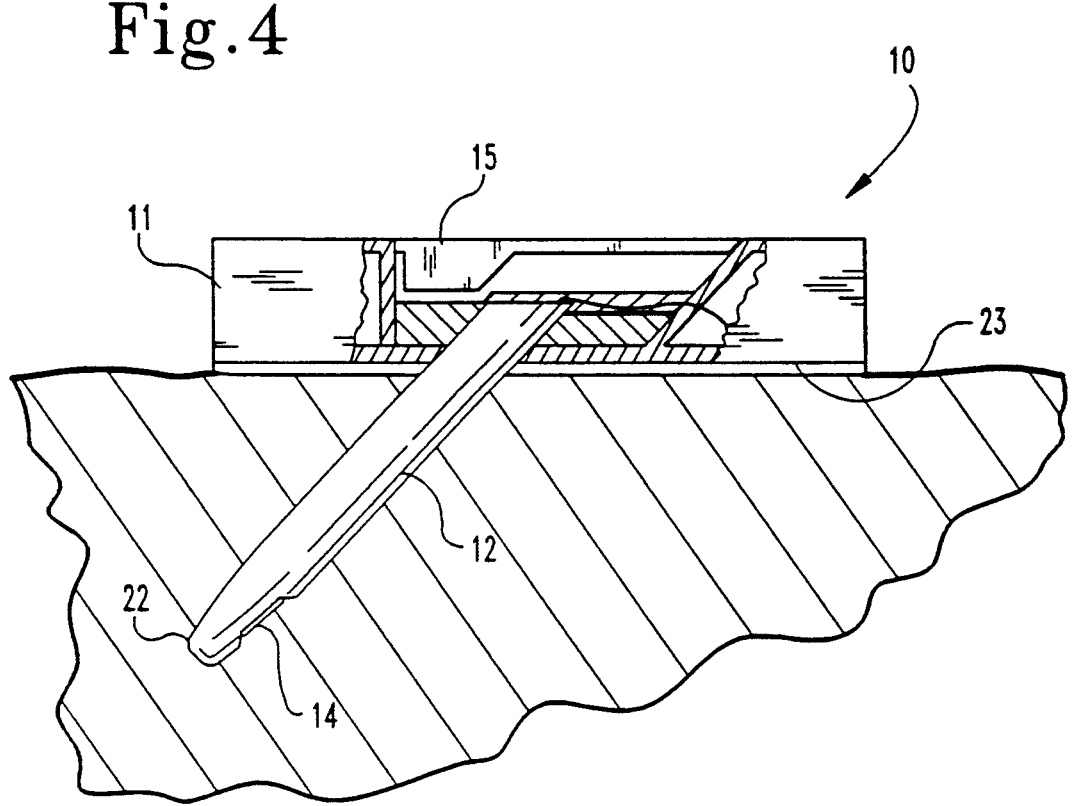
FIG. 4 is a side, partially cross-sectional view of the apparatus of FIG. 1 upon use for implantation of a sensor subcutaneously, and particularly showing the apparatus with the needle removed and the cover in the closed position.
Figure 3:
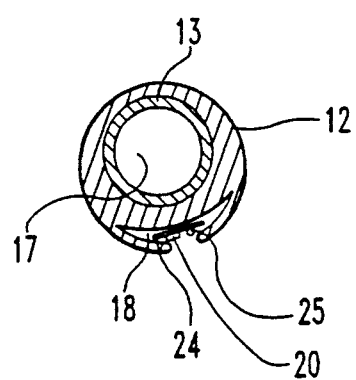
FIG. 3 is a cross-sectional view of the dual-lumen tube useful in the present invention, taken along the line 3—3 in FIG. 1 and looking in the direction of the arrows.

In practice, the apparatus 10 is grasped by its housing 11 and the needle is forced through the skin. The closely conforming tube 12 is carried through the skin by the introducing needle and the distal end of the tube is thereby positioned beneath the skin surface. After placement of the tube, the cover 15 is opened and the needle is removed from the tube by use of handle 16. The cover is then closed (FIG. 4). The bottom surface of the housing is preferably provided with an adhesive layer 23 to attach the housing to the skin upon implantation of the sensor.

The sensor 14 may be any of a variety of sensors which is intended for in vivo use and which is adapted for implantation by use of the apparatus and method described. For example, the sensor may be a glucose sensor such as described in R. J. Morff, D. Lipson, K. W. Johnson, J. J. Mastrototaro, C. C. Andrew, A. R. Potvin, "Reproducible Microfabrication of Electroenzymatic Glucose Sensors on a Flexible Substrate," *Proc. 1st World Congress on Biosensors*, (May 2-4, 1990); and J. J. Mastrototaro, K. W. Johnson, R. J. Morff, D. Lipson, C. C. Andrew, "An Electroenzymatic Glucose Sensor Fabricated on a Flexible Substrate," *Proc. Third International Meeting on Chemical Sensors*. (Sep. 24-26, 1990), the disclosures of which are incorporated herein by reference. The glucose sensors described therein are sized and configured to be conveniently received within the second lumen 18.

Means are provided for communicating information from the sensing element to a location spaced from the sensing element. The sensor preferably includes a flexible substrate upon which are mounted the sensing elements and wires communicating therewith. In this embodiment, the sensing element 20 is preferably positioned within the opening 19, and the substrate 24 and supported wires 25 together extend from the sensing element through the second lumen 18. The wires and substrate exit the tube adjacent its proximal end. A filler 26 may be used to assist in securing the tube to the housing, and also to contain the wires 25 exiting from the proximal end of the tube. These wires are connected with means for receiving information from the sensing element, which means may be located conveniently within the housing 11. Alternatively, the wire leads may be connected to an external device, in which case a connector (not shown) may be included. Such means, whether internal or external, may further be provided for displaying and/or recording the sensed information.

The apparatus is simple and readily produced. The components may be formed from a variety of known materials suitable for medical applications, particularly biocompatible materials useful for production of the needle, dual-lumen tube and the like which are inserted under the skin. Typical materials for the tube 12 include polyethylene, polytetrafluoroethylene, polyurethane and silicone, the last one providng greater flexibility. Sizing of the apparatus is determined by the nature of the sensors to be used and the required placement of the sensors subcutaneously. In a typical example, the tube 12 comprises 19 gauge tubing, and a 21 to 27 gauge syringe needle is used in the circular central lumen.

The apparatus and method of the present invention provide for the quick, simple and accurate placement of an in vivo sensor. The system is easily used without the need for medical personnel. Consequently, the implantation can be performed conveniently at home or elsewhere. The needle provides rigidity during implantation, but upon removal the tube has flexibility desirable to reduce local irritation and to increase user comfort.

The apparatus may be provided in sterile packaging, and the user simply removes the apparatus and performs the implantation as described. The apparatus either includes the necessary recording/displaying means, or a connector is provided for coupling the wire leads to a suitable, external monitoring device.

While the invention has been described in detail in the foregoing description, the same is to be considered as illustrative and not restrictive in character, it being understood that only the preferred embodiment has been described and that all changes and modifications that come within the spirit of the invention are desired to be protected.

What is claimed is:

1. An apparatus for implantation of a sensor beneath the skin surface which comprises:
   a housing;
   a dual-lumen tube having a proximal end attached to said housing and having a distal end projecting from said housing, said tube, including the distal end, defining a first lumen and a second lumen;
   a needle received within the first lumen of said tube, said needle including a proximal end and a pointed distal end extending outwardly of the distal end of said tube; and a sensor received within the second lumen of said tube, said sensor including a sensing element positioned within the second lumen adjacent the distal end of said tube and outside of said housing, said sensor further including means for communicating information sensed by the sensing element to a location spaced from the sensing element, whereby implantation of said sensor is accomplished by forcing said needle and said tube into a desired location beneath the skin surface.

2. The apparatus of claim 1 in which said sensor is a glucose sensor.

3. The apparatus of claim 1 in which the means for communication includes a wire lead extending from the sensing element through the second lumen to the proximal end of said tube.

4. The apparatus of claim 3 in which said housing includes means for receiving information from the sensing element and displaying information concerning the sensed condition.

5. The apparatus of claim 1 in which said tube includes an opening at the distal end exposing a portion of the second lumen, the sensing element being positioned within the opening to be exposed exteriorly of said tube.

6. The apparatus of claim 5 in which the means for communicating includes a wire lead extending from the sensing element through the second lumen to the proximal end of said tube.

7. The apparatus of claim 1 in which said needle is removeably received by the first lumen, said needle including means for removal of said needle from the first lumen.

8. The apparatus of claim 7 in which the means for removal includes a handle attached to the proximal end of said needle.

9. The apparatus of claim 8 in which said housing defines a cavity and in which the handle of said needle is received within the cavity.

10. The apparatus of claim 9 in which said housing further includes a cover having a first position closing the cavity and a second position opening the cavity, the handle of said needle being receivable within the cavity with the cover in the closed position, said needle being removeable from said tube and housing with the cover in the open position.

11. The apparatus of claim 1 in which said tube includes a distal end having an exterior surface which is tapered inwardly in the distal direction.

12. The apparatus of claim 1 in which the second lumen is crescent-shaped.

13. The apparatus of claim 1 and which further includes means for securing said housing to a support surface.

14. The apparatus of claim 13 in which said housing includes a bottom surface from which said tube projects, said means for securing including adhesive material located on the bottom surface of said housing.

15. A method for implantation of a sensor beneath the skin surface which comprises the steps of:

a. providing an implanting device which includes a housing, a dual-lumen tube having a proximal end attached to the housing and having a distal end projecting from the housing, the tube, including the distal end, defining a first lumen and a second lumen, a needle received within the first lumen of the tube, the needle including a proximal end and a pointed proximal end extending outwardly of the distal end of the tube, and a sensor received within the second lumen of the tube, the sensor including a sensing element positioned within the second lumen adjacent the distal end of the tube and outside of the housing, the sensor further including means for communicating information sensed by the sensing element to a location spaced from the sensing element; and, b. pressing the needle through the skin surface to position the distal end of the tue to a desired location beneath the skin surface.

16. The method of claim 15 and which further includes, after step b, the step of removing the needle from the tube.

17. The method of claim 16 in which the needle includes a handle, the removing of the needle comprising pulling on the handle to remove the needle from the tube.

18. The method of claim 15 and which further includes, after step b, the step of securing the housing to the skin surface.

19. The method of claim 18 in which the housing includes a bottom surface from which the tube projects, the bottom surface including an adhesive coating, the step of securing the housing comprising adhering the bottom surface of the housing to the skin surface.

20. The method of claim 18 and which further includes, after step b, the step of removing the needle from the tube.

21. The method of claim 15 in which step b. comprises positioning the distal end of the tube in a location within the subcutaneous tissue.

* * * * *